(12) United States Patent
Radspieler

(10) Patent No.: US 11,224,525 B2
(45) Date of Patent: Jan. 18, 2022

(54) PROSTHESIS COVER FOR A PROSTHESIS, PARTICULARLY FOR AN ARTIFICIAL LEG

(71) Applicant: Romedis GMBH, Neubeuern (DE)

(72) Inventor: Andreas Radspieler, Neubeuern (DE)

(73) Assignee: ROMEDIS GMBH, Neubeuern (DE)

( * ) Notice: Subject to any disclaimer, the term of this patent is extended or adjusted under 35 U.S.C. 154(b) by 0 days.

(21) Appl. No.: 16/766,767

(22) PCT Filed: Dec. 4, 2018

(86) PCT No.: PCT/EP2018/083407
§ 371 (c)(1),
(2) Date: May 26, 2020

(87) PCT Pub. No.: WO2019/110543
PCT Pub. Date: Jun. 13, 2019

(65) Prior Publication Data
US 2021/0000620 A1    Jan. 7, 2021

Related U.S. Application Data

(63) Continuation of application No. PCT/EP2018/083407, filed on Dec. 2, 2018.

(30) Foreign Application Priority Data

Dec. 5, 2017    (DE) .................... 10 2017 128 838.4

(51) Int. Cl.
*A61F 2/78*    (2006.01)
*A61F 2/50*    (2006.01)

(52) U.S. Cl.
CPC .... *A61F 2/7812* (2013.01); *A61F 2002/5001* (2013.01); *A61F 2002/503* (2013.01); *A61F 2002/7837* (2013.01)

(58) Field of Classification Search
CPC ..... A61F 2/78; A61F 2/712; A61F 2002/5001
See application file for complete search history.

(56) References Cited

U.S. PATENT DOCUMENTS 4,479,272 A    10/1984    Beldzisky
4,908,037 A    3/1990    Ross
(Continued)

FOREIGN PATENT DOCUMENTS

DE    3028381 A1    2/1982
DE    9300615 U1    3/1993
(Continued)

OTHER PUBLICATIONS

International Search Report and Written Opinion for PCT/EP2018/083407 dated Mar. 19, 2019.
(Continued)

*Primary Examiner* — Bruce E Snow
(74) *Attorney, Agent, or Firm* — Millman IP Inc.

(57) ABSTRACT

The present invention relates to a prosthesis covering (100) with a closed cross-section which comprises a first section (10), a second section (20) and a third section (30). The second section (20) is arranged in longitudinal direction between the first section (10) and the third section (30) and consists of other material than the other two sections. The second section (20) may optionally at least in a first subsection (21) be folded, doubled over, raised, lamella-like or multi-layer.

5 Claims, 5 Drawing Sheets

(56) References Cited

U.S. PATENT DOCUMENTS

| | | | | |
|---|---|---|---|---|
| 5,133,775 A | * | 7/1992 | Chen .......................... | A61F 2/60 2/16 |
| 5,593,453 A | * | 1/1997 | Ahlert ....................... | A61F 2/78 2/270 |
| 5,728,052 A | | 3/1998 | Meehan | |
| 9,539,119 B2 | * | 1/2017 | Sauer ........................ | A61F 2/78 |
| 2007/0150069 A1 | | 6/2007 | Takami et al. | |
| 2011/0059291 A1 | | 3/2011 | Boyce et al. | |
| 2013/0331952 A1 | | 12/2013 | Halldorsson et al. | |
| 2015/0081038 A1 | | 3/2015 | Rauch | |
| 2015/0265431 A1 | | 9/2015 | Egilsson et al. | |

FOREIGN PATENT DOCUMENTS

| | | |
|---|---|---|
| DE | 10040955 A1 | 3/2002 |
| DE | 202010017462 U1 | 12/2011 |
| DE | 102012022484 A1 | 5/2014 |
| DE | 102016113590 A1 | 2/2017 |
| EP | 0985388 A2 | 3/2000 |
| GB | 2067074 A | 7/1981 |
| GB | 2357725 A | 7/2001 |
| WO | 2013072064 A1 | 5/2013 |
| WO | 2019110543 A1 | 6/2019 |

OTHER PUBLICATIONS

German Search Report for German Patent Application No. 10 2017 128 838.4 dated Jul. 26, 2018.

* cited by examiner

PROSTHESIS COVER FOR A PROSTHESIS, PARTICULARLY FOR AN ARTIFICIAL LEG

The present invention relates to a prosthesis covering according to claim 1 having a closed cross-section, i.e. for slipping or putting the extremity in, for example the leg.

From practice prosthesis coverings are known, which are placed on the skin and in particular over a patient's joint in order to bridge it.

An object of the present invention is to suggest a further prosthesis covering.

The object according to the present invention is achieved by a prosthesis covering having the features of claim 1.

Hereby, the prosthesis covering comprises along its longitudinal extension at least or exactly one first, second and third section or consists thereof. Thereby, the second section is arranged in longitudinal direction between the first and the third section and is made of or comprises a material with a higher E-Modul (Young's modulus) than that of the materials of the first and the third section.

During its intended use, the prosthesis covering serves to cover an extremity prosthesis, in particular a leg prosthesis, at least in sections. As intended, the prosthesis covering may rest, on the one hand, directly or separated by at least one material layer on the limb stump and, on the other hand, directly or separated by at least one material layer on a section of the prosthesis, for example a cosmetic supplement. Thereby, the prosthesis covering may bridge, cover or surround an artificial joint of the prosthesis.

In all of the following statements, the use of the expression "may be" or "may have", and so on, is to be understood synonymously with "preferably is" or "preferably has", and so on, respectively, and is intended to illustrate embodiments according to the present invention.

Embodiments according to the present invention may comprise one or several of the above-mentioned or following features. Thereby, the features mentioned herein may in any combination be subject-matter of embodiments according to the present invention unless the person skilled in the art recognizes a specific combination as technically impossible.

Embodiments according to the present invention are further subject-matter of the dependent claims and embodiments.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed by the present invention as the interpretation that a numerical word, for example, "one" may alternatively mean "exactly one", wherever this is evidently technically possible for the person skilled in the art. Both are encompassed by the present invention and apply herein to all used numerical words.

Whenever an embodiment is mentioned herein, it is then an exemplary embodiment according to the present invention.

Herein, the information "above" and "below" are to be understood, in case of doubt by the person skilled in the art, as absolute or relative spatial information which relates to the orientation of the component in question during its intended use.

In some embodiments, the second section comprises at least a first subsection which in at least one state thereof is folded.

A prosthesis covering, as used herein, may also be a sealing covering, protective cover, vacuum(knee)bandage, cuff, prosthesis cuff, prosthesis liner. Interchanging these terms will lead in any case to combinations of features which are also encompassed by the present invention.

In several embodiments, the prosthesis covering is not a liner. It is optionally not intended to be worn under a prosthesis shaft. It is intended to be worn over the prosthesis.

In some embodiments, the second section comprises at least one first subsection which is pleated/doubled over in at least one state of the prosthesis covering. In other embodiments, the prosthesis cover and in particular the second section does not comprise a pleated/folded/doubled over subsection and/or bellows.

A doubled over subsection may be understood as a subsection in which material that forms the subsection or is involved in its formation is arranged at least in sections in two layers one above the other. Thereby, two layers of the material, that form the wall of the subsection, lie on top of each other; this can e.g. be compared to a folding. Unfolding of the subsection may lead to a greater length (e.g. in a direction transverse to the direction of the fold) of the subsection. Thereby, the doubling over/folding over would be more or less dispensed with and would completely disappear when the subsection is completely unfolded. When unfolded completely, the subsection may only be single layer, depending on its design.

An example for a doubling over is known from the accordion. However, the width of the area in which the layers of the material lie in folds on top of each other thereby usually extends transverse to the longitudinal direction of the bellows. According to the present invention, the width in which the layers of the material lie in folds on top of each other extends entirely, predominantly or substantially in the longitudinal direction of the subsection or of the prosthesis covering.

In several embodiments, a layer of the wall is to be understood as the whole thickness of the, for example textile, wall. When the wall is folded, it then lies in layers on top of each other. Layers, as used herein, may in several embodiments are not to be confused with the layers which make up the wall. A wall can comprise several layers, for example, an inner layer consisting of a very skin-friendly material or comprising such, and a very waterproof and airtight material that lies on top of the inner layer forming an outer layer. Thereby, when the wall is smoothed out, the outer and the inner layer form a single layer. Only when the wall is folded, so that—from the inside to the outside—an inner layer, an outer layer, a further outer layer, an inner layer and finally an outer layer adjoin each other, would one refer herein to a wall as being in two layers or doubled over.

Above-mentioned statements referring to the inner and the outer layer may, in some embodiments, also be transferred to the inner or the outer side, respectively.

In several embodiments, the wall of the first, the second and/or the third section is made of exactly one layer.

In some embodiments, the second section comprises at least one first subsection which is folded/raised in at least one state of the prosthesis covering.

In several embodiments, the second section comprises at least one first subsection which is lamella-like in at least one state of the prosthesis covering.

In some embodiments, the second section comprises at least one first subsection which is completely or at least in sections multi-layer in at least one state of the prosthesis covering.

In further embodiments, the second section comprises at least one structure extending in longitudinal direction or at least also in longitudinal direction of the prosthesis covering. The structure is—preferably as such or in itself—not folded, not doubled over, not raised, not lamella-like or not multi-layer.

In several embodiments, all or some of the lamellas, multi-layer sections or doubled over sections extend in circumferential direction preferably not in the longitudinal direction of the prosthesis covering nor of the second section.

In some embodiments, the first, second and/or third section of the prosthesis covering comprises or consists of an airtight material.

In several embodiments, the first subsection and/or the second subsection of the second section of the prosthesis covering are not elastic.

In some embodiments, the first and/or the third section of the prosthesis covering are elastic.

In several embodiments, the term "non-stretchable" or "non-elastic" means that the Young's modulus, abbreviated as E-Modul, of the relevant subsection is at least higher than 700 N/mm$^2$, preferably higher than 1000 N/mm$^2$, most preferably higher than 2000 N/mm$^2$.

In certain embodiments, the term "non-stretchable" or "non-elastic" means that a stretching of the relevant subsection may be not more than 20%, preferably not more than 10%, preferably not more than 5%, most preferably not more than 2% of its length, before the subsection breaks.

In several embodiments, the relevant subsection or fibres thereof have a Young's modulus the same as Nylon.

In certain embodiments, "stretchable" or "elastic" means the opposite of "non-stretchable" or "non-elastic". A fabric or a body is, therefore, either stretchable or elastic, or non-stretchable or non-elastic.

In several embodiments the second section of the prosthesis covering comprises in at least one subsection thereof a, textile for example, elevated structure on its inner side, i.e. the side of the prosthesis covering or of the second section facing the body extremity while wearing the prosthesis covering.

In certain embodiments, the prosthesis covering or the second section provides a material reserve in longitudinal direction of the prosthesis covering.

The material reserve may be 10%, 20%, 30%, 40% or more, for example, when comparing the completely folded with the completely unfolded state. Therefore, a prosthesis covering or its second section may be extended/lengthened by unfolding by one of the above-mentioned percentages, or values in-between. Thereby, the unfolding is due preferably not or essentially not to elastic material properties, but rather to the unfolding, for example lamellas.

In some embodiments, the prosthesis covering does not comprise a closed end. In others, it comprises a closed end.

In several embodiments, the prosthesis covering comprises one or more elasticized fabrics, in others, not.

In some embodiments, not every element or not every section of the prosthesis covering comprises elasticized fabrics.

In several embodiments, not every element or not every section of the prosthesis covering comprises fabrics that display a higher elastic stiffness in one direction than in the other direction, extending orthogonal to this one direction.

In some embodiments, the inner surface of the prosthesis covering is not covered and/or not completely covered by a silicone elastomer material, in particular not with a continuously, hardened silicone elastomer material.

In several embodiments, the second section of the prosthesis covering does not comprise a gel.

In several embodiments, the prosthesis covering does not comprise a gel.

In several embodiments, the prosthesis covering is not a joint bandage to be pulled over, does not consist of an elastic tube with a front side and a flexor side opposite to it, wherein the flexor side is at least in sections made of two layers, wherein the elastic tube is assembled from a front part and a rear part, wherein the rear part forms the flexion side.

In some embodiments, the prosthesis covering does not comprise, at its flexor side, flat-knitted sections between which tubular circular knitted fabrics are knitted in, which are arranged in the flexion area.

In several embodiments, the prosthesis covering is not a joint bandage with a tubular main body made of an elastic textile material with an insert in the flexion area, whereby the elasticity of the insert is higher than the elasticity of the main body.

In some embodiments, the prosthesis covering does not comprise an insert with two areas displaying different elasticity, the elasticities of which are each higher than the elasticity of the main body.

In several embodiments, the prosthesis covering is not a structure with surfaces made of textile threads having at least a transverse wave structure designed on one side, which is elastically pre-tensioned or stabilized by an elastic fabric arrangement that is integrated or arranged under a covering structure and which is connected to the covering structure in predetermined spacings.

In some embodiments, the prosthesis covering does not comprise a textile laminate with an elastic textile basis and a plastic coating arranged on it, the plastic coating being thinner than the textile basis and having a perforation integrated in order to adjust an adapted elasticity of the textile laminate.

In several embodiments, the prosthesis covering does not comprise any added pieces. This includes in particular attached, e.g. glued or sewn-on, parts, patches, pads or cushions.

In some embodiments, the prosthesis covering is not a compression bandage, in particular not for wearing it on or over the healthy knee, above all, when pressure should be applied to the knee by a middle section of the prosthesis covering.

In several embodiments, the prosthesis covering does not comprise fabric grain orientations, in particular no sections with different fabric grain orientations.

In some embodiments, the prosthesis covering does not comprise protrusions on its inner side and/or its outer side.

In several embodiments, the prosthesis covering does not comprise on its inner side and/or on its outer side material that is provided to prevent a movement of the prosthesis covering on the skin or of a layer arranged over the skin.

In several embodiments the prosthesis covering comprises exactly three sections which are connected to each other by gluing, stitching or by other means in order to form a tubular structure.

In several embodiments, the first, second and third section are each circumferential. Therefore, they each form a closed structure forming a through-opening into which the prosthesis or the stump of the patient is inserted, or through which the stump is guided.

In some embodiments, the first, second and third section are each circumferentially air-permeable.

In several embodiments, the prosthesis covering, the first, the second and/or the third section are each single-layer.

In several embodiments, the first and/or the third section, but preferably not the second section, comprise or consist of a material that allows a stretching of the relevant section in its circumferential direction.

However, the elasticity of this section in a direction perpendicular to the circumferential direction (i.e. in the longitudinal direction of the prosthesis covering) is lower, in the range between 0% up to 70% of the elasticity in circumferential direction, for example. Elasticity may be achieved purely by way of example by fibres running in a wavy or zig-zag pattern in the circumferential direction together with e.g. fibres not running in a wavy or zig-zag pattern in the longitudinal direction.

In several embodiments, the prosthesis covering does not comprise a curvature in its longitudinal direction.

In some embodiments, the prosthesis covering comprises stiffening elements made of a strap/tape-like material. The stiffening elements may be sewn on, glued on or connected in another way to the fabric or the material of the prosthesis covering.

In several embodiments, the wall of the second section—e.g. in a completely unfolded state thereof—does not comprise a variable radial thickness, especially of its wall, particularly not over the anterior side.

In some embodiments, the prosthesis covering does not comprise a bulge resulting from the use of different materials or material thicknesses, in none of the sections.

In several embodiments, the prosthesis covering or one or more sections are not made of a knitted, single-piece elastic tube.

In some embodiments, the prosthesis covering does not comprise a fabric section which is stretchable in two, particularly perpendicular, directions.

In several embodiments, the prosthesis covering does not comprise a material that restrains movement, optionally neither on the inner side nor on the outer side.

In some embodiments, the prosthesis covering comprises no plurality of annular protrusions.

In several embodiments, the prosthesis covering does not comprise, at least at its outer side, any protrusions running longitudinally, which are each longitudinally distributed around the circumference of the prosthesis covering.

In some embodiments, the prosthesis covering does not comprise, at least at its outer side, any stabilizing element, in particular not a stabilizing element made of plastic.

In several embodiments, the prosthesis covering does not comprise any knitware and/or any knitted fabric or does not consist of such.

In some embodiments, the prosthesis covering does not comprise a ring or a plurality of rings on its inner surface.

In several embodiments, there are no sticking or adhesive fibres integrated in the fabric, which protrude on the inner side of the prosthesis covering in order to ensure additional hold.

In some embodiments, the prosthesis covering is suitable and designed for creating a vacuum. Therefore, the material of the prosthesis covering, in particular of the second section, may be an airtight material, such that a created vacuum may be maintained at least for a specific period, for example, several hours or days.

In several embodiments according to the present invention, at least one diameter and/or circumference (or the average diameter or circumference, respectively) of the first section and/or the third section is, in an unstressed state or in a state of non-use of the prosthesis covering, smaller than a diameter and/or circumference (or the average diameter or circumference, respectively) of the second section. The diameter or the circumference of the second section may optionally be larger by between 5% and 20% than the diameter or circumference of the first and/or the third section.

Some or all embodiments according to the present invention may comprise one, several or all of the advantages mentioned above and/or in the following.

It may be of advantage that the prosthesis covering, when it is put on the patient in order to bridge a joint, may provide a high level of comfort when being worn, due to a material reserve which the prosthesis covering provides the wearer, for example on its anterior side, by the second section. Therefore, depending on the design of the second section, no force or only a low amount of force is required in comparison to common prosthesis coverings, when bending the joint covered or bridged by the prosthesis covering, e.g. the artificial knee when walking.

A rubbing on the skin or on a layer lying under the prosthesis covering, e.g. a liner, which is caused by stretching the prosthesis covering on the extensor side of the joint followed by a contraction of the prosthesis covering over or on the prosthesis or the skin of the patient, may also be advantageously prevented or reduced as the second section lying on the extensor side of the joint is not elastic or only elastic to a comparatively low degree.

Additionally, due to the Young's modulus of the prosthesis covering, it may be ensured that the prosthesis covering does not exert pressure onto the underlying structures or tissues, independent of a bending of the joint, at least in the area of the section which is non-elastic or only elastic to a comparatively low degree.

The present invention is exemplarily explained with regard to the accompanying drawing in which same reference numerals refer to the same or similar components. In the figures the following applies:

FIG. 1 shows a prosthesis covering 100 according to the present invention in a first embodiment in a side view with a slight perspective from above.

The prosthesis covering 100 comprises a first section 10, a second section 20 and a third section 30, or alternatively consists thereof. Its longitudinal direction or longitudinal axis is indicated with L. The prosthesis covering 100 extends in an axial direction. The transverse direction or the radial direction extends perpendicular to the longitudinal direction L.

Figure 1:
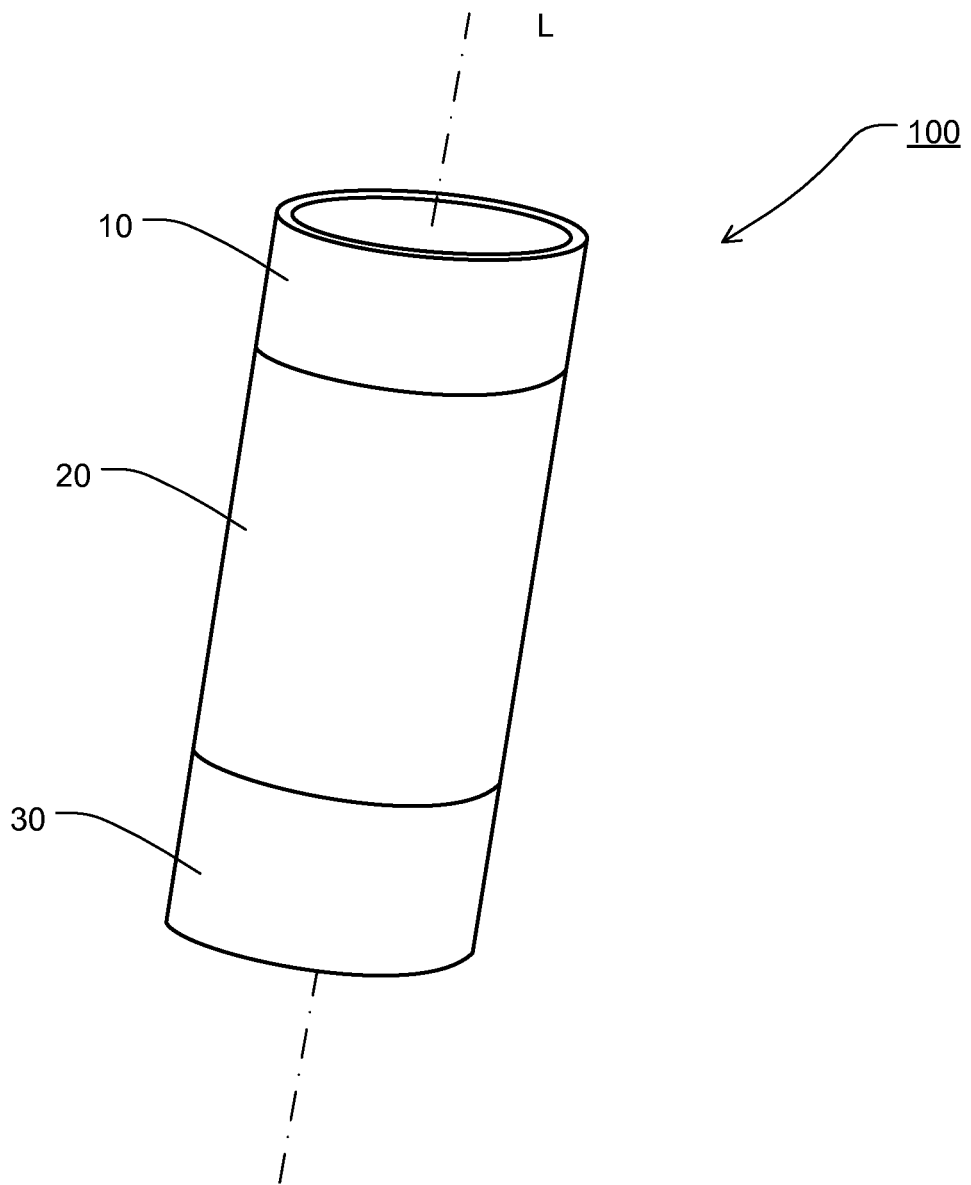
FIG. 1 shows a prosthesis covering according to the present invention in a first embodiment.

Thereby, the second section 20 is arranged between the first section 10 and the third section 30. In the example of the figures the first section 10 and the third section 30 are not in contact with each other. As in FIG. 1, they are optionally in at least a radial layer, not in contact with each other.

The second section 20 comprises a higher E-Modul (Young's modulus) than the first section 10 and/or than the third section 30.

Figure 2:
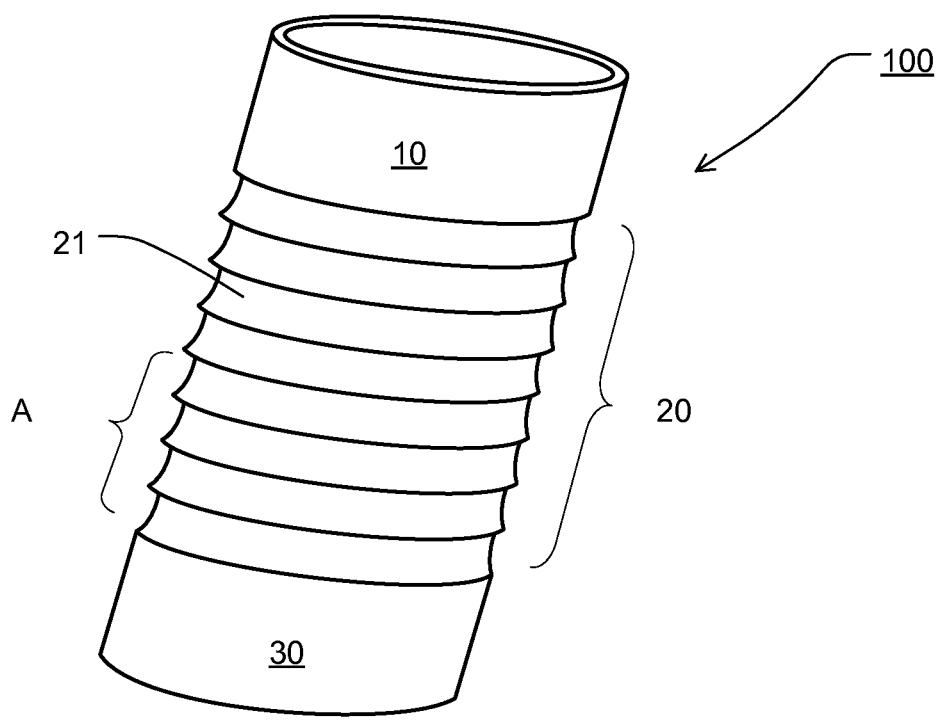
FIG. 2 shows a prosthesis covering according to the present invention in a second embodiment.

FIG. 2 shows a prosthesis covering 100 according to the present invention in a second embodiment.

Thereby, in a first subsection 21 thereof, the second section 20 is folded lamella-like along its entire circumference. In FIG. 2 there are shown, for example, eight lamellas, any other number is equally encompassed by the present invention.

The lamellas serve as a material reservoir. When the prosthesis covering 100 is put over a joint, for example the artificial knee joint, and the patella or the artificial patella of the wearer of the prosthesis covering 100 is pointing to the left with regard to FIG. 2 (with the popliteal fossa (hollow of the knee) on the right side of the prosthesis covering 100 with respect to FIG. 2), the second section 20 with a higher Young's modulus than sections 10 and/or 30 may be extended/lengthened by unfolding, e.g. over the knee.

Hereby, the patient feels no pressure on the skin which would result from the tension of an elastic material in the second section 20. The second section 20 (in comparison to a lower Young's modulus of the first and/or the third section 30) does not allow such pressure to occur. Instead of building up pressure, it simply lengthens (extends) in the longitudinal direction due to the lamella-like structure provided therefore.

Figure 2A:
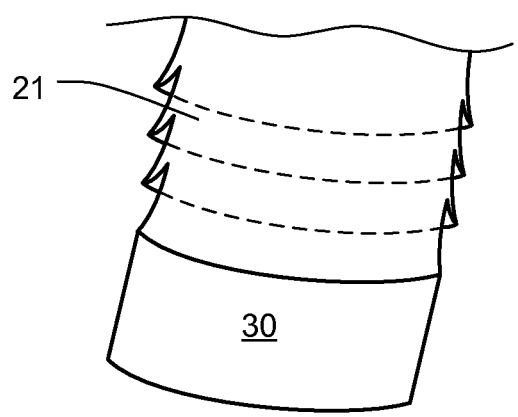
FIG. 2a shows the lower section of the prosthesis covering according to the present invention of FIG. 2 in a partial sectional view.

FIG. 2a shows the lower section of the prosthesis covering 100 according to the present invention of FIG. 2 in a partial sectional view A. The section shown in FIG. 2a is indicated with the reference numeral A in FIG. 2.

It is visible, that the material of the first subsection 21 of the second section 20, which is folded in lamellas, lies on top of each other due to a double over. In the state of the prosthesis covering 100 shown in FIG. 2 and FIG. 2a, the material is still doubled over on itself or still comprises doubled over parts, however, the main extension of them lies (more or less) parallel to the longitudinal axis of the prosthesis covering 100, in the embodiment shown, however, not perpendicular to it.

Figure 3:
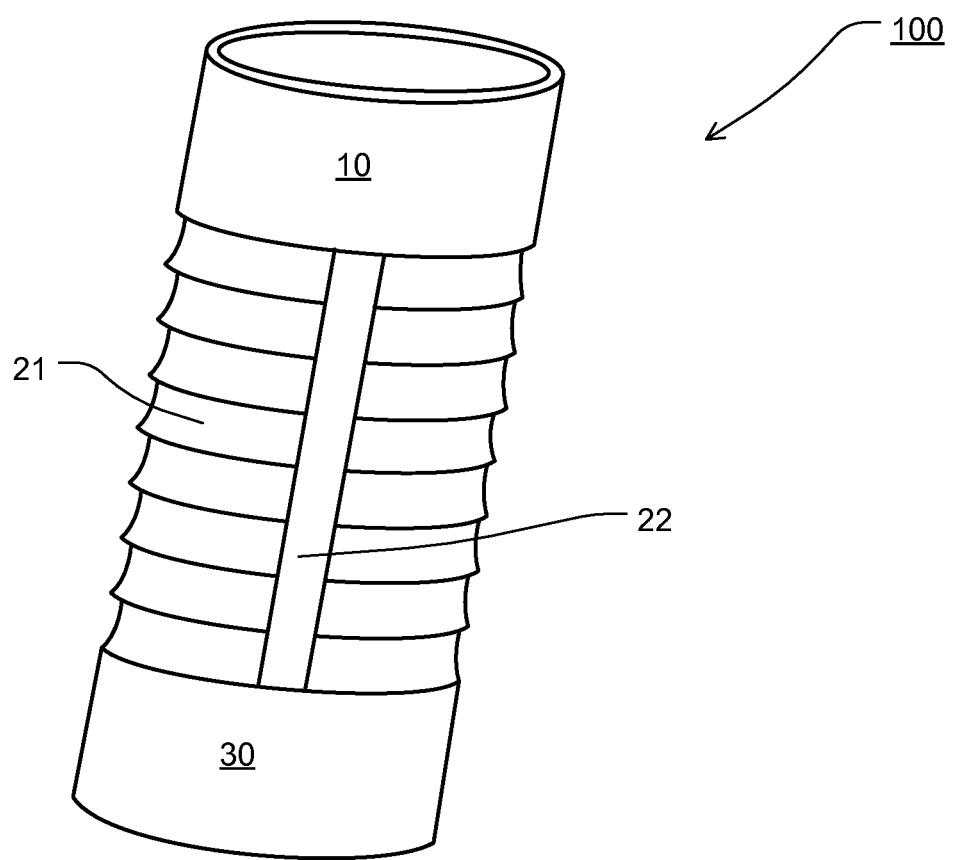
FIG. 3 shows a prosthesis covering according to the present invention in a third embodiment.

FIG. 3 shows a prosthesis covering 100 according to the present invention in a third embodiment.

The prosthesis covering 100 differs from the one in FIG. 2 in having a second subsection 22.

The second subsection 22 connects the first section 10 with the third section 30. It may ensure that the distance between the first section 10 and the third section 30 (in longitudinal direction L) does not exceed a maximum distance. It may further ensure that the material reservoir of the second section 20 does not unfold while the prosthesis covering is being pulled on or put on and is no longer available to the patient during later flexion movements.

Unlike the first subsection 21, the length or the visible length of which may be increased by unfolding, the second subsection 22 does not comprise a material reserve. Its length is unchangeable, however, within its elasticity.

Thereby, the second subsection 22 may be less elastic in comparison to the elasticity of the first section 10 and/or the third section 30. It may optionally be non-elastic.

In FIG. 3 a second subsection 22 can be seen. However, two or more of such second subsections 22 may be provided distributed over the circumference of the prosthesis covering 100.

Also, the width of the second subsection 22 may vary. In FIG. 3 the second subsection 22 is shown comparatively narrow. Alternatively, it may be wider than shown in FIG. 3. It may constitute e.g. up to 100°, 120°, 140°, 160° or 180° or more of the circumference of the prosthesis covering 100. The latter embodiment is shown in FIG. 4.

Figure 4:
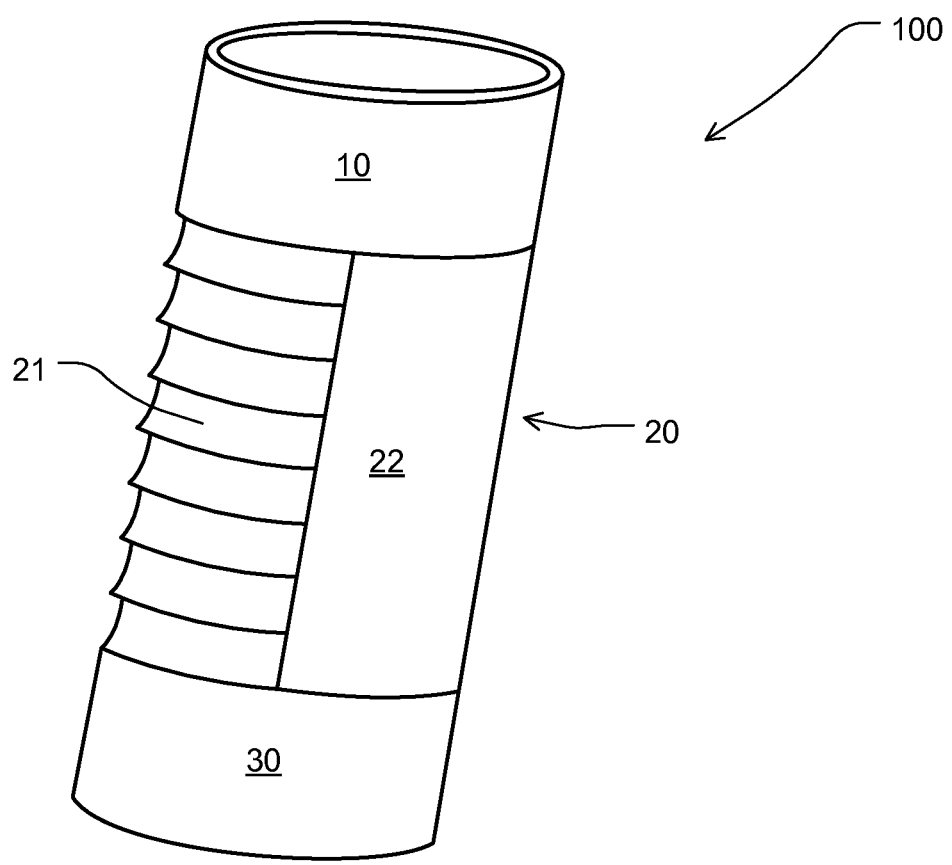
FIG. 4 shows a prosthesis covering according to the present invention in a fourth embodiment.

FIG. 4 shows a prosthesis covering 100 according to the present invention in a fourth embodiment.

The prosthesis covering 100 corresponds to the one shown in FIG. 3, except that there is only one second subsection 22, which extends over 180° of the circumference of the prosthesis covering 100.

The first subsection 21 may be optionally supplemented to 360° with the second subsection 22, as shown by way of example in FIG. 4.

The first subsection 21 may cover 360° of the circumference of the extremity or of the prosthesis covering 100. The second subsection 22 may lie on or adjacent to the first subsection 21, optionally at its inner or outer surface.

As shown in FIG. 4 by way of example, the first subsection 21 may constitute or cover 180° of the circumference of the prosthesis covering 100. It may alternatively also be wider than shown in FIG. 4. Thus, it may constitute e.g. up to 240° or more of the circumference of the prosthesis covering 100.

In any embodiment according to the present invention, the first subsection 21 may cover between 40% and 70% of the circumference, more preferably a part of the circumference, constituting between 55% and 65% of the circumference, most preferably 60% of the circumference.

The percentages mentioned above may optionally refer to the unstressed state of the prosthesis covering 100, for example, before use, e.g. in the shipping packaging, or it may refer to a state of use, for example, on the extremity.

Figure 5:
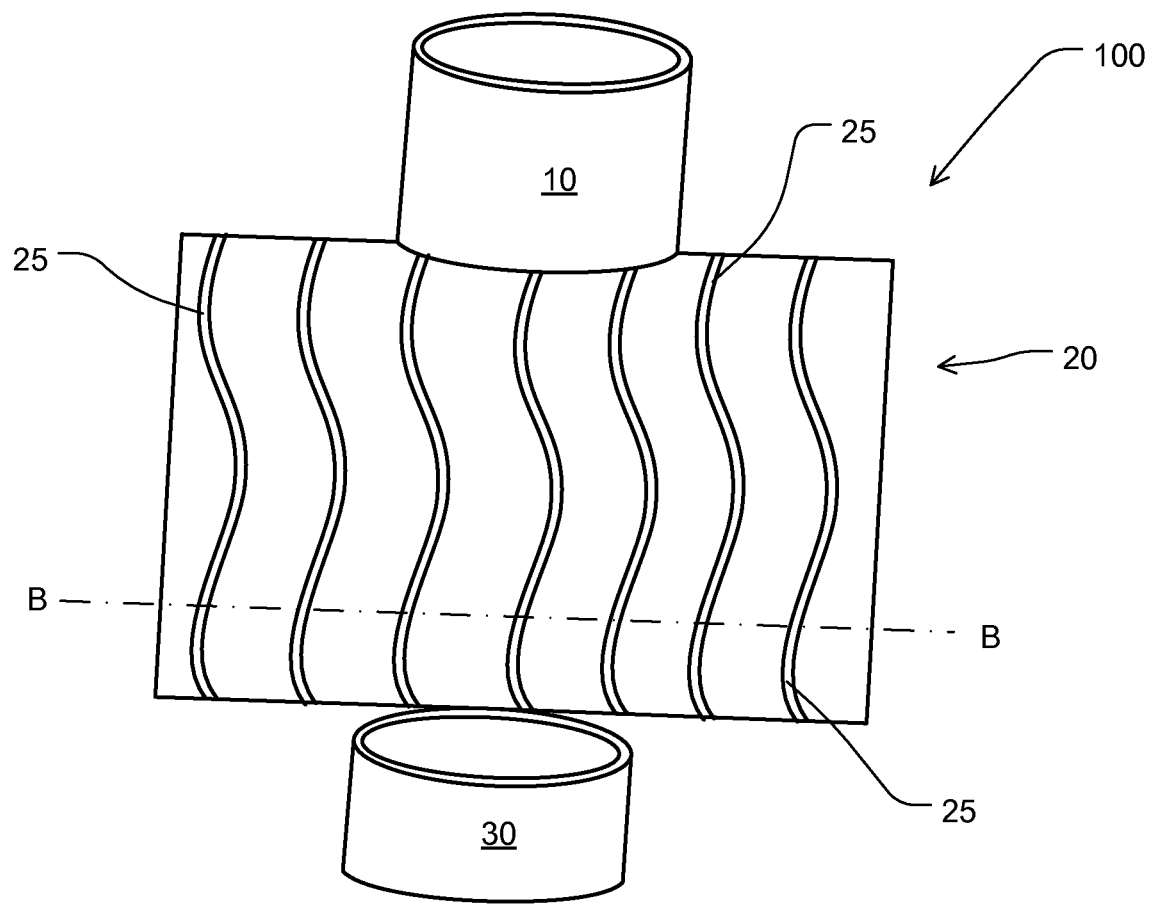
FIG. 5 shows a prosthesis covering according to the present invention in a fifth embodiment.

FIG. 5 shows a prosthesis covering 100 according to the present invention in a fifth embodiment in a partial sectional view.

Only the second section 20 is cut and unfolded, but not the first section 10 nor the third section 30. The view to the drawing plane of FIG. 5 shows the inner side of the second section 20, which would be in contact with the skin of the patient during the use of the prosthesis covering 100 or, nevertheless, would be facing it.

An elevated or prominent structure 25 may be recognized, which extends away from the inner side of the second section 20 and during use of the prosthesis covering 100 extends radially into the prosthesis covering 100.

The structure 25 may preferably extend in a longitudinal direction of the prosthesis covering 100. It serves to prevent the second section 20 from lying completely planar on the patient's body. Benefited by the distance the structure 25 keeps open between the inner side of the second section 20 and the patient's body (e.g. the skin), a negative pressure between the inner side of the second section 20 and the patient's body may be established by suitable negative pressure devices without any relevant niche formations.

Figure 5A:
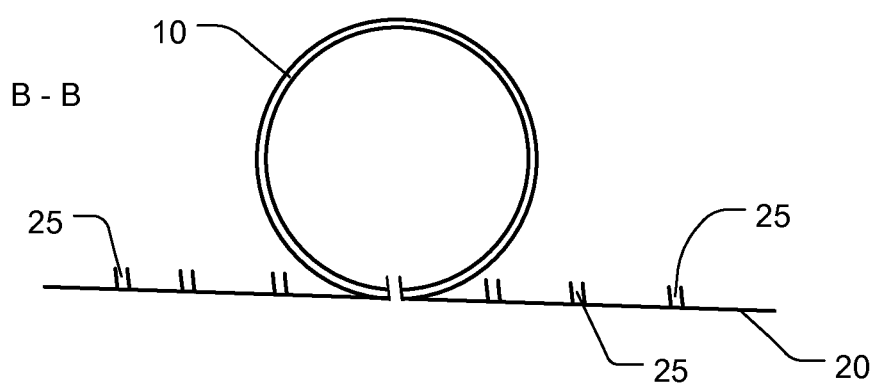
FIG. 5a shows a section through the prosthesis covering according to the present invention of FIG. 5 along a line B-B of FIG. 5.

FIG. 5a shows the single cut through the prosthesis covering 100 according to the present invention of FIG. 5 along a line B-B of FIG. 5.

REFERENCE NUMERALS 100 prosthesis covering
10 first section
20 second section
21 first subsection
22 second subsection
25 elevated structure
30 third section

The invention claimed is:

1. A prosthesis covering having a closed cross-section,
wherein the prosthesis covering comprises along its longitudinal extension at least a first section, a second section and a third section;
wherein the second section includes a material comprising a higher E-Modul (Young's modulus) than at least one of a material of the first section and a material of the third section;
wherein the second section is arranged between the first section and the third section;
wherein the second section includes a first subsection which in at least one state thereof is in sections folded, doubled over, raised, lamella-like or multiple-layer;
wherein the second section comprises, as a second subsection, a structure extending in a longitudinal direction of the prosthesis covering or of the second section, wherein the second subsection is not folded, doubled over, raised, lamella-like or multi-layer; and
wherein the second subsection lies on or adjacent to the inner or outer surface of the first subsection or complements together with the first subsection to 360° of the circumference.

2. The prosthesis covering according to claim 1, wherein at least one of the first section, the second section and the third section is made of, or comprises, an airtight material.

3. The prosthesis covering according to claim 1, wherein at least one of the first subsection and the second subsection is not elastic.

4. The prosthesis covering according to claim 1, wherein at least one of the first section and the third section is elastic.

5. The prosthesis covering according to claim 1, wherein the second section, in at least one subsection thereof, comprises an elevated structure on its inner side.

* * * * *